United States Patent
Souid (10) Patent No.: US 11,467,151 B1
(45) Date of Patent: Oct. 11, 2022

(54) PHOSPHORESCENCE OXYGEN ANALYZER AND USES THEREOF

(71) Applicant: UNITED ARAB EMIRATES UNIVERSITY, Al Ain (AE)

(72) Inventor: Abdul-Kader Souid, Manlius, NY (US)

(73) Assignee: UNITED ARAB EMIRATES UNIVERSITY, Al Ain (AE)

( * ) Notice: Subject to any disclaimer, the term of this patent is extended or adjusted under 35 U.S.C. 154(b) by 0 days.

(21) Appl. No.: 17/561,210

(22) Filed: Dec. 23, 2021

(51) Int. Cl.
*G01N 33/50* (2006.01)
*G01N 21/64* (2006.01)

(52) U.S. Cl.
CPC ..... *G01N 33/5014* (2013.01); *G01N 21/6428* (2013.01); *G01N 33/5082* (2013.01); *G01N 2201/021* (2013.01); *G01N 2201/0231* (2013.01); *G01N 2201/062* (2013.01)

(58) Field of Classification Search
CPC ........... G01N 33/5014; G01N 21/6428; G01N 33/5082; G01N 2201/021; G01N 2201/0231; G01N 2201/062
See application file for complete search history.

(56) References Cited

U.S. PATENT DOCUMENTS

| | | |
|---|---|---|
| 4,810,655 A | 3/1989 | Khalil et al. |
| 5,593,899 A * | 1/1997 | Wilson ............... A61B 5/14552 436/127 |
| 9,121,827 B2 | 9/2015 | Mayer et al. |
| 10,194,804 B2 | 2/2019 | Zuckerman |
| 2006/0002822 A1* | 1/2006 | Papkovsky .......... G01N 31/225 422/82.08 |
| 2008/0051646 A1 | 2/2008 | Papkovsky et al. |

(Continued)

FOREIGN PATENT DOCUMENTS

CA 1309876 C 11/1992

OTHER PUBLICATIONS

Amao et al., "An oxygen sensing system based on the phosphorescence quenching of metalloporphyrin thin film on alumina plates", Analyst (2000), 125.9, pp. 1601-1604.

(Continued)

*Primary Examiner* — Marcus H Taningco
(74) *Attorney, Agent, or Firm* — Nath, Goldberg & Meyer; Richard C. Litman (57) ABSTRACT

The phosphorescence oxygen analyzer has a light source including an LED array that flashes light at 1,000 flashes per second. The light flashes are received in a test chamber containing a carousel having a plurality (preferably ten) of sample vials mounted thereon. The samples a phosphorescent probe (palladium(II) complex, namely, meso-tetra-(4-sulfonatophenyl)tetrabenzoporphyrin; Pd phosphor) mixed with either a control sample of tissue or a sample of tissue and a suspected toxin or a pharmaceutical it is desired to test, the carousel being rotated to irradiate each vial in turn. The probe has an absorption maximum at 625 nm and emission maximum at 800 nm. Phosphorescent emissions are detected by a photomultiplier tube connected to a measurement 2020 board, which is connected to a processor that computes the lifetime and peak of the pulses, which determines the rate of phosphorescent decay due to oxygen metabolized by the tissue mitochondria.

16 Claims, 4 Drawing Sheets

(56) References Cited

U.S. PATENT DOCUMENTS

| | | | |
|---|---|---|---|
| 2015/0241494 A1* | 8/2015 | Miyanaga | G01R 31/2837 324/613 |
| 2018/0271411 A1 | 9/2018 | Ashkenazi | |
| 2021/0163869 A1* | 6/2021 | Sweet | C12M 29/14 |
| 2021/0330946 A1* | 10/2021 | Miller | G01F 1/662 |
| 2022/0072273 A1* | 3/2022 | Dove | A61K 49/0017 |

OTHER PUBLICATIONS

Borisov et al., "New Optical Sensors for Oxygen Based on Phosphorescent Cationic Water-Soluble Pd(II), Pt(II), and Rh(III) Porphyrins", Journal of Analytical Chemistry (2004), 59.2, pp. 155-159 (Abstract only).

Al-Jasmi et al., "Phosphorescence Oxygen Analyzer as a Measuring Tool for Cellular Bioenergetics", Bioenergetics, In Tech (2011) pp. 237-256.

Kondrashina, "New Phosphorescence Based Probes and Techniques for the Analysis of Cellular Oxygen and Respiration", Thesis, University College Cork (2014) (Abstract only).

Al-Samri et al., "Measurement of oxygen consumption by murine tissues in vitro", Jounall of Pharmacological and Toxicological Methods (2011), pp. 196-204.

Whyte et al., "Cannabinoids Inhibit Cellular Respiration of Human Oral Cancer Cells", Pharmacology (2010), 85. pp. 328-335.

Shaban et al., "Oxygen measurements via phosphorescence", Computer Methods and Programs in Biomedicine (2010. 100, pp. 265-268.

Tao et al., "Kinetic Studies on Enzyme-Catalyzed Reactions: Oxidation of Glucose, Decomposition of Hydrogen Peroxide and Their Combination", Biophysical Journal (2009), vol. 96, pp. 2977-2988.

AL-jasmi et al., "The phosphorescence oxygen analyzer as a screening tool for disorders with impaired lymphocyte bioenergetics", Molecular Genetics and Metabolism (2011), 104, pp. 529-536.

\* cited by examiner

PHOSPHORESCENCE OXYGEN ANALYZER AND USES THEREOF

BACKGROUND

1. Field

The disclosure of the present patent application relates to instruments for assessing tissue respiration, and particularly to an improved phosphorescence oxygen analyzer and uses thereof, including improvements to enable the machine to assess more rapidly occurring cellular metabolism and new uses for the instrument.

2. Description of the Related Art

The 'phosphorescence oxygen analyzer' has been extensively used to monitor 'cellular mitochondrial oxygen consumption' in tissues. This analytic tool has aided the assessment of cellular bioenergetics and addressed important research queries in biological chemistry, such as in vitro investigations of cellular responses to drugs and toxins. In this system, oxygen concentration is determined from the phosphorescence decay rate ($1/T$, the negative of the slope of phosphorescence decay curve) of the palladium (II) complex, meso-tetra-(4-sulfonatophenyl)-tetrabenzoporphyrin (Pd phosphor). This chemical probe has an absorption maximum at 625 nm and an emission maximum at 800 nm. The process of detection is based on oxygen quenching of the phosphorescence of Pd phosphor. Typically, samples are exposed to light flashes (10 per sec) from a pulsed light-emitting diode array with a peak output at 625 nm (OTL630A-5-10-66-E, Opto Technology, Inc, Wheeling, Ill.). Emitted phosphorescent light is detected by a Hamamatsu photomultiplier tube (PMT #928) after passing through a filter centered at 800 nm. The measurements are calibrated with β-glucose and glucose oxidase system [μ-glucose+$O_2$ glucono-δ-lactone+$H_2O_2$]. The calibration reaction contains phosphate-buffered saline (PBS), 3 μM Pd phosphor, 0.5% fat-free albumin, 50 μg/mL glucose oxidase and various concentrations of β-glucose. The values of $1/\tau$ ($\mu sec^{-1}$) are linear with dissolved oxygen concentration: $1/\tau=1/\tau_o+k_q[O_2]$, where $1/\tau$=the phosphorescence decay rate in the presence of oxygen, $1/\tau_o$=the phosphorescence decay rate in the absence of oxygen, and $k_q$=the second-order oxygen quenching rate constant (in $\mu sec^{-1}$ $\mu M^{-1}$). For air-saturated solution ([$O_2$]=230 μM), the values (mean±SD) of $1/\tau=0.00277\pm0.00012$ $\mu sec^{-1}$ (n=684) and of $\tau=362\pm17$ μsec (median, 361). For oxygen-depleted solution ([$O_2$]=0 μM), the values of $1/\tau=0.00178\pm0.000073$ $\mu sec^{-1}$ (n=1,722) and of $\tau=606\pm59$ μsec (median, 600). This gives an estimated value for $k_q$ of $4.3\times10^{-6}$ $\mu sec^{-1}$ $\mu M^{-1}$.

Cellular respiration is measured in 1-mL sealed vials. Mixing is carried out with the aid of parylene-coated stirring bars. The respiratory substrates are endogenous metabolic fuels with or without added glucose. In cell suspensions sealed from air, [$O_2$] decreased linearly with time, showing the zero-order kinetics of cellular respiration. The rate of respiration (k, in μM $O_2$ $min^{-1}$) is the negative of the slope $d[O_2]/dt$. Cyanide inhibited the decline of [$O_2$] with time, confirming oxygen is consumed in the mitochondrial respiratory chain.

Briefly, the term cellular respiration (cellular mitochondrial oxygen consumption) describes the delivery of oxygen to mitochondria, breakdown of reduced metabolic fuels in the respiratory chain, passage of electrons to oxygen, and resulting synthesis of ATP. Impaired cellular respiration implies any break in these steps.

Dissolved oxygen concentration ([02]) in air-saturated freshwater at sea level and 30° C. (salinity=0.0 ppt) is 160 mm Hg, 5.3 mL/L, 7.6 mg/L, or 237.5 μM (mole $O_2$ weight in mg÷mole $O_2$ volume in mL=32÷22.4=1.4286).

While the existing phosphorescence analyzer has proven useful for many purposes, it is believed that the analyzer's capabilities may be increased by improving the instruments capacity to measure metabolic reactions that occur at a faster rate and by making it easier to measure serial samples more quickly. Also, there are some new uses for the analyzer that haven't been reported earlier.

Thus, a phosphorescence oxygen analyzer and uses thereof solving the aforementioned problems is desired.

SUMMARY

The phosphorescence oxygen analyzer has a light source including an LED array that flashes light at 1,000 flashes per second. The light flashes are received in a test chamber containing a carousel having a plurality (preferably ten) of sample vials mounted thereon. The samples a phosphorescent probe (palladium(II) complex, namely, meso-tetra-(4-sulfonatophenyl)tetrabenzoporphyrin; Pd phosphor) mixed with either a control sample of tissue or a sample of tissue and a suspected toxin or a pharmaceutical it is desired to test, the carousel being rotated to irradiate each vial in turn. The probe has an absorption maximum at 625 nm and emission maximum at 800 nm. Phosphorescent emissions are detected by a photomultiplier tube connected to a measurement 2020 board, which is connected to a processor that computes the lifetime and peak of the pulses, which determines the rate of phosphorescent decay due to oxygen metabolized by the tissue mitochondria.

The rate of flashes produced by the light source enables testing metabolic processes that occur in the submillisecond and microsecond time scale. The analyzer has a high speed mixer using a technology similar to "resonant acoustic mixing" (RAM) to assure a rate compatible with the LED flashes. The temperature inside the test chamber will be controlled efficiently to ±0.1° C. by a precision incubator to enable testing the effect of temperature on the reaction.

The phosphorescence oxygen analyzer has a multitude of uses. It is anticipated that these new features will expand the capabilities of the instrument to enable studying such events as: (1) studying changes in cellular oxygen consumption associated with fertilization (reproduction). Changes in dissolved oxygen concentration will be monitored when an 'egg cell' (e.g., from a frog) is mixed with 'sperms'; (2) neutrophil oxygen burst; neutrophil release of 'reactive oxygen species' in response to pathogen products (e.g., lipopolysaccharides). This tool will be used to study impaired neutrophil oxygen burst, such as in chronic granulomatous disease (CGD); (3) studying changes in cellular oxygen consumption in various organs in the presence of various concentrations and exposure times to drugs, toxins, and other chemical compounds; (4) monitoring and studying oxygen producing and oxygen consuming chemical and biochemical reactions; (5) studying mitochondrial cell death pathway (apoptosis); (6) studying changes in cellular mitochondrial oxygen consumption in various human and animal diseases, such as murine retinal oxygen consumption in diabetic retinopathy; and (7) studying compatibility of compounds (e.g., nanoparticles) with cellular mitochondrial oxygen consumption in various tissues.

Moreover, it has recently been discovered that the phosphorescence oxygen analyzer, even as presently constituted, can be used to assess the affect of such neurotoxins as rotenone and 1-methyl-4-phenylpyridinium on cellular respiration in striatal tissue, which may serve as a biomarker for assessing the adverse effects of such toxins, as described below. In addition, the phosphorescence oxygen analyzer has been used to study spinal cord bioenergetics in mice afflicted with autoimmune encephalomyelitis, an exemplary lesion of multiple sclerosis, also as described below.

These and other features of the present subject matter will become readily apparent upon further review of the following specification.

BRIEF DESCRIPTION OF THE DRAWINGS

Similar reference characters denote corresponding features consistently throughout the attached drawings.

DETAILED DESCRIPTION OF THE PREFERRED EMBODIMENTS

The phosphorescence oxygen analyzer has a light source including an LED array that flashes light at 1,000 flashes per second. The light flashes are received in a test chamber containing a carousel having a plurality (preferably ten) of sample vials mounted thereon. The samples contain β-glucose and a phosphorescent probe (palladium(II) complex, namely, meso-tetra-(4-sulfonatophenyl)tetrabenzoporphyrin; Pd phosphor) mixed with either a control sample of tissue or a sample of tissue and a suspected toxin or a pharmaceutical it is desired to test, the carousel being rotated to irradiate each vial in turn. The probe has an absorption maximum at 625 nm and emission maximum at 800 nm. Phosphorescent emissions are detected by a photomultiplier tube connected to a measurement 2020 board, which is connected to a processor that computes the lifetime and peak of the pulses, which determines the rate of phosphorescent decay due to oxygen metabolized by the tissue mitochondria.

Basically, the phosphorescence oxygen analyzer measures the concentration of oxygen in solution. It does this by taking advantage of the phenomenon that the presence of oxygen in solution quenches phosphorescent emissions from the Pd(II) complex, and does so in a manner that is linearly proportional to the concentration of oxygen in solution with the Pd phosphor probe, i.e., $1/\tau = 1/\tau_o + k_q[O_2]$, where $1/\tau$ is the phosphorescence decay rate in the presence of $O_2$, $1/\tau_o$ is the phosphorescence decay rate in the absence of $O_2$, and $k_q$ is the second-order $O_2$ quenching rate constant in $sec^{-1} \mu M^{-1}$.

Figure 1:
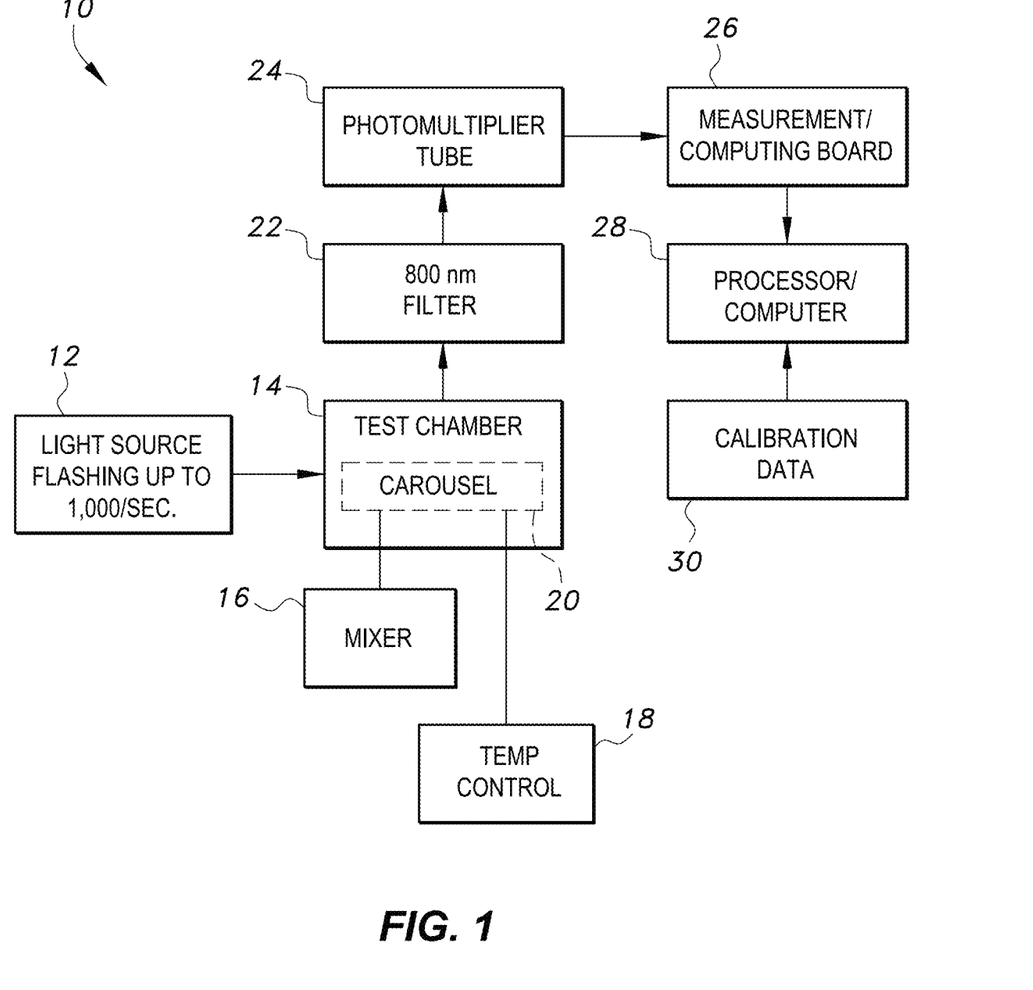
FIG. 1 is a block diagram of a phosphorescence oxygen analyzer.

As shown in FIG. 1, the phosphorescence oxygen analyzer 10 includes a light source 12 capable of flashing pulses of light at a controlled rate of up between one second and 1,000 pulses per second, which is two orders of magnitude faster than the current rate of 10 pulses per second. Such light sources are currently available, and have been used in such devices as tachistoscopes and tachometers, for example. Operation at such high speeds would enable the study of metabolic reactions that occur in the submillisecond and microsecond time scale.

The flashes of light may be directed towards sealed test vials disposed in a test chamber 14 having transparent walls or walls with transparent windows for receiving the pulses of light from the light source 12 and emitting the resulting phosphorescent emissions to a detector, the vials containing tissue samples and a phosphorescent probe ((palladium(II) complex, namely, a palladium II complex of meso-tetra-(4-sulfonatophenyl)tetrabenzoporphyrin; Pd phosphor), and may also contain albumin and phosphate-buffered saline (PBS) or other solvent. In order to accommodate the higher speed permitted by the new light source, the contents of the vials are mixed by a high speed, more efficient mixer 16. The mixer 16 may make use of "resonant acoustic mixing" technology (originally described in U.S. Pat. No. 7,188,993, issued to Howe et al. on Mar. 13, 2007) to mix the contents of the vial at speeds consistent with the LED flashes of the new light source 12.

A temperature control 18 including a precision incubator is connected to the test chamber 14 in order to metabolic reactions of the tissue in the sample vials under different environmental conditions of temperature and pressure. The sample vials may be mounted on a carousel 20 in the test chamber 14 in order to rotate the sample vials into the path of the light source for convenience and increased speed and efficiency in testing multiple samples. The use of precision incubators with test chambers and carousels for rotating samples in test equipment is known in test instruments and need not be described further.

Phosphorescent emissions from the probe in the sample vials pass through a transparent wall (or transparent window in the wall) of the test chamber 14 and through a filter 22 centered at 800 nm and are detected by a photomultiplier tube 24, such as a Hamamatsu PMT R955 (made by Matsusada Precision, Inc, Japan), which converts light received from the test chamber to an electrical signal and greatly amplifies the current proportional to the intensity of the light, resulting in an analog signal with peaks corresponding to the pulses of light. The analog signal from the photomultiplier tube 24 is received by a measurement/computing board 26, such as a USB-2020 board (2-channel, 12-bit, 20 MS/s, 64 MS memory, 8-DIO, AD9225), which is an analog-to-digital converter converting the analog output of the photomultiplier tube 24 to a digital stream of pulses, and includes counters for counting the pulses and measuring their peak voltage and duration.

The output of the measurement/computing board 26 is passed to a processor/computer 28, which may be a microcontroller, programmable logic controller, or other processing device capable of running software, but is preferably a computer having a microprocessor programmed to run software for analyzing the data. The software program was developed using Microsoft Visual Basic 6 (VB6) programming language, Microsoft Access Database 2007 (Access) database management system, and Universal Library components developed by the electronic board company, Measurement Computing, for use with Microsoft Visual Basic 6 programming language. The software utilizes a relational database that stores experiments, pulses and pulse metadata, including slopes. Pulse identification is performed by detecting ten phosphorescence intensities above 1.0 volt (by default). Peak identification is performed by the program, which detects the highest 10% data points of a pulse and chooses the point in the group that is closest to the pulse's decay curve. Depending on the sample rate, a minimum number of data points per pulse is set and used as a cutoff to remove invalid pulses with too few data points.

The developed program provides full control and customization of the data acquisition, storage and analysis. The choices of VB6 and Access as programming and storage environments are due to their availability, simplicity, widespread use and VB6 components that read directly from the PCI card made available by Measurement Computing. The processor/computer 28 has access to calibration data 30 obtained from a glucose-glucose oxidase system in which measurements of dissolved oxygen are made by a YSI 6050020 Pro20 Handheld Dissolved Oxygen Meter.

The phosphorescence oxygen analyzer has a multitude of uses. As shown in the following examples, it has recently been discovered that the phosphorescence oxygen analyzer, even as presently constituted, can be used to assess the affect of such neurotoxins as rotenone and 1-methyl-4-phenylpyridinium on cellular respiration in striatal tissue, which may serve as a biomarker for assessing the adverse effects of such toxins. In addition, the phosphorescence oxygen analyzer has been used to study spinal cord bioenergetics in mice afflicted with autoimmune encephalomyelitis, an exemplary lesion of multiple sclerosis, also as described below.

Example 1

Effect of rotenone and 1-methyl-4-phenylpyridinium on cellular respiration in striatal tissue Pd(II) meso-tetra (sulfophenyl) tetrabenzoporphyrin sodium salt ($C_{60}H_{32}N_4Na_4O_{12}PdS_4$; catalog #T41161) was purchased from Frontier Scientific (Logan, Utah, USA). Its solution (2.5 mg/mL, or 2.0 mM) was dissolved in $dH_2O$ and stored at $-20°$ C. All other reagents were purchased from Sigma-Aldrich (St. Louis, Mo.). Glucose oxidase (10 mg/mL) was dissolved in $H_2O$ and stored at $-20°$ C. Rotenone (2.0 mM) was dissolved in absolute ethanol and stored at $-20°$ C.; its final concentration was determined using molar extinction coefficient at 294 nm of 19,200. 1-Methyl-4-phenylpyridinium iodide (MPP+, molecular weight 297.13) was purchased from Sigma Aldrich, USA. The stock solution of MPP+(50 mM) was prepared by dissolving 29.71 mg in 2.0 mL sterile $dH_2O$; aliquots of the solution were stored at $-80°$ C.

C57BL6 male mice (13 weeks old, about 20 g weight) were housed at $22°$ C. with 60% humidity and 12-h light-dark cycles. Rodent chow and filtered water were provided ad libitum. The study was approved from the UAE University Animal Research Ethics Committee (Ref. ERA-20196026). Diethyl ether was used for anesthesia.

The studied mice were not treated in any way prior to striatal tissue collection. The skin and skull were cut to expose the whole brain, which was then rapidly removed and placed in a freshly prepared Pd phosphor solution: Phosphate-buffered saline (PBS: 137 mM NaCl, 2.7 mM KCl, 4.3 mM $Na_2HPO_4$, and 1.4 mM $KH_2PO_4$, pH 7.4), 3.0 µM Pd phosphor, 0.5% fat-free albumin, with and without 5.0 mM glucose. The brain region that contained the striatum was dissected. The specimen weight was determined prior to placing it in the oxygen measuring vial that contained 2.0 mL of the Pd phosphor solution. A small portion of the specimen was stored at $-80°$ C. for Western blot analysis.

The tissue specimens were analyzed by Western blots. Briefly, the samples were homogenized in a glass homogenizer using 5.0 µL per mg of Radio-immunoprecipitation Assay Buffer (20-188 Millipore) that contained phosphatase and protease inhibitors (Thermo Scientific, Rockford, Ill., USA). The homogenates were centrifuged at $4°$ C. (14,000 rpm for 10 min). Total protein content in the whole cell lysates was determined using the bicinchoninic acid protein assay (Thermo Scientific, Rockford, Ill., USA). Twenty µg of the whole cell lysate was separated by electrophoresis, which was then transferred to PVDF (polyvinylidene difluoride) membrane. After blocking in 5% skimmed milk for one hour at $25°$ C., the blot was incubated overnight at $4°$ C. with the mouse monoclonal anti-tyrosine hydroxylase (TH) antibody with a dilution of 1:1000 (ImmunoStar, WI, USA). After washing with PBS-T, the membrane was probed for one hour at $25°$ C. with horseradish peroxidase (HRP)-conjugated goat anti-mouse secondary antibody with a dilution of 1:20,000 (Jackson ImmunoResearch, PA, USA). The bands of interest were visualized using a West Pico Chemiluminescence kit (Thermo Scientific, Rockford, Ill., USA). The blots were stripped and re-probed for GAPDH (1:1000; polyclonal Rabbit, Cell Signaling Technologies, USA) as a loading control. Only samples positive for TH were used in this study.

For oxygen analysis, our previously described phosphorescence oxygen analyzer was used to monitor oxygen consumption at $25°$ C. in the studied striatal fragments. In reaction vials sealed from air, oxygen concentration decreased linearly with time (zero-order kinetics); the rate (k, in µM $O_2$ $min^{-1}$) was thus the negative of d $[O_2]$/dt. The calibration reactions utilized glucose oxidase (D-glucose+ $O_2 \rightarrow$ D-glucono-δ-lactone+$H_2O_2$) and µ-glucose. Dissolved oxygen in the solution was also depleted by the addition of glucose oxidase plus µ-glucose. Potassium cyanide (KCN, added from a stock prepared in $dH_2O$ immediately before use) inhibited respiration, confirming oxygen was consumed in cytochrome oxidase.

Figure 2A:
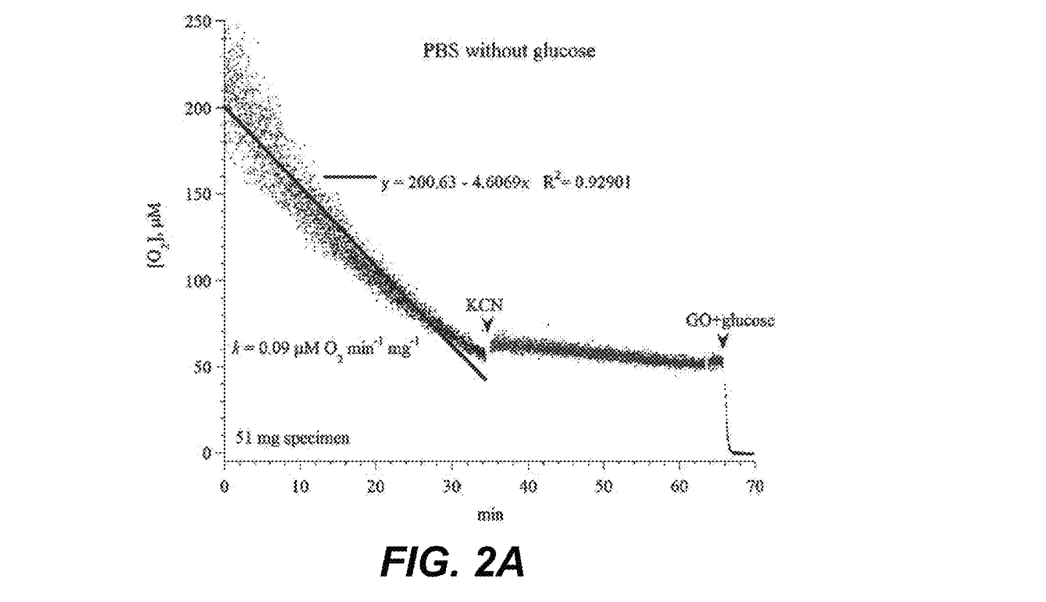
FIG. 2A is a plot of oxygen concentration vs. time without glucose.
Figure 2B:
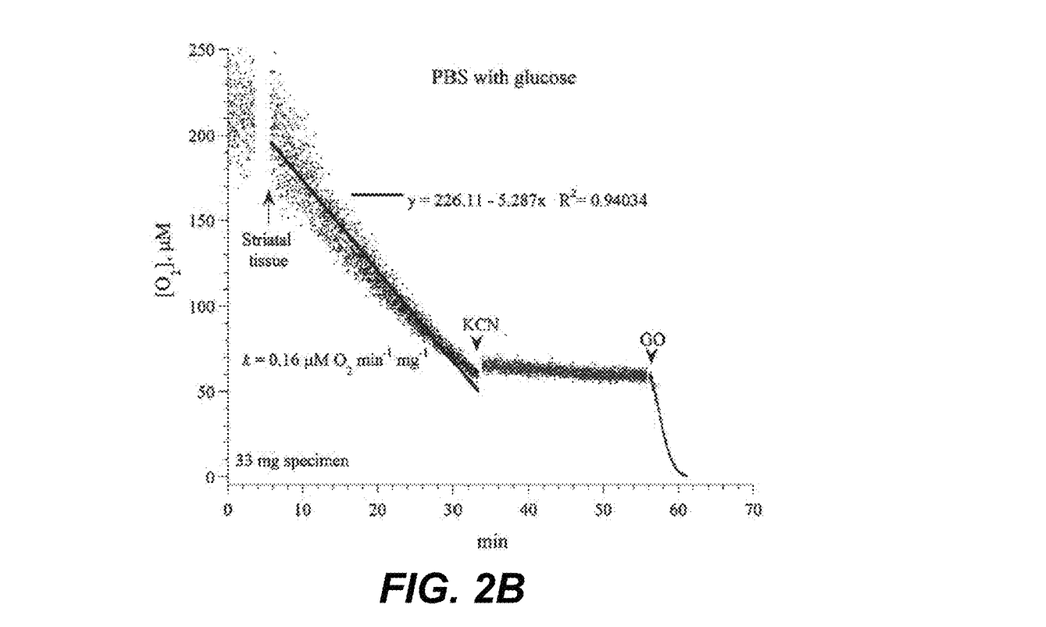
FIG. 2B is a plot of oxygen concentration vs. time with glucose.

Striatal cellular respiration was studied in the Pd phosphor solution (the PBS solution described above) with and without 5.0 mM glucose. The results are shown in FIGS. 2A and 2B. In both conditions, the decline in oxygen concentration was linear with time. The linear fit, however, was better in the presence of glucose than without glucose ($R^2$, 0.94304 versus 0.92901). The rate of respiration (k, in µM $O_2$ $min^{-1}$ $mg^{-1}$) without glucose (oxidations driven by the endogenous nutrients) slowed down after 28 min, likely reflecting limited nutrients. It was also faster in the presence of glucose than without glucose (k, 0.16 versus 0.09). Thus, the presence of glucose (i.e., oxidations driven by both endogenous nutrients and cellular influx of glucose) improved both the rate and linearity of striatal respiration. The overall value of k (mean t SD) in the presence of glucose was: 0.141 t 0.041 µM $O2$ $min^{-1}$ $mg^{-1}$ (n=7). The addition of potassium cyanide (KCN) resulted in >90% inhibition of respiration. Thus, the 'cyanide insensitive respiration' was <10%. These results confirmed that oxygen was reduced by cytochrome oxidase. The addition of glucose oxidase (GO) depleted remaining oxygen in the solution.

It is also well to know that the linear decline of oxygen concentration with time signified zero-order kinetics of oxygen reduction by cytochrome oxidase (i.e., a constant amount of oxygen was consumed per min) and assured a reasonable striatal tissue viability during the measurements.

Figure 3A:
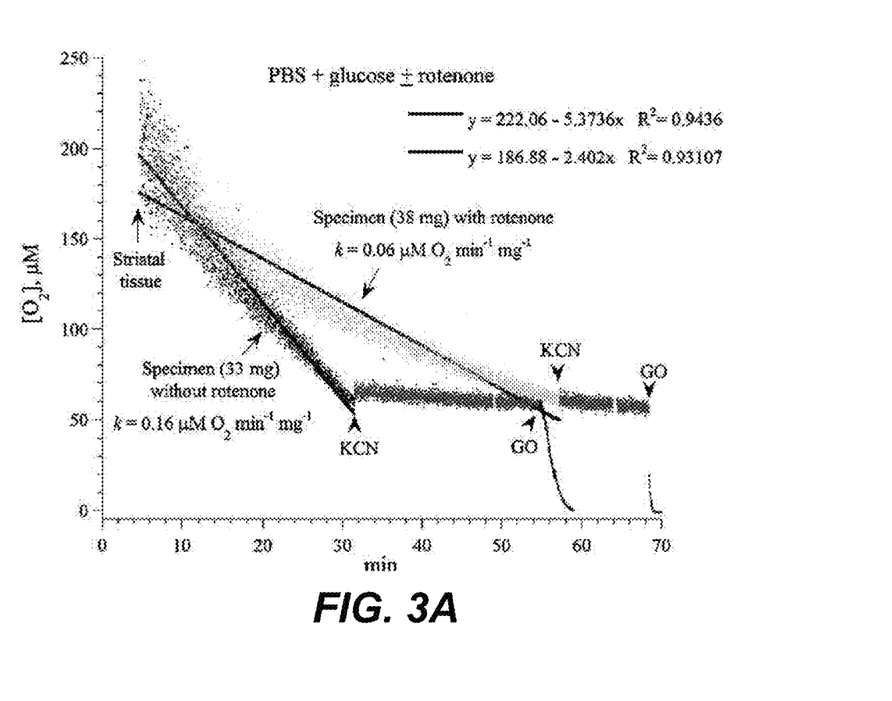
FIG. 3A is a plot of oxygen concentration vs. time without glucose and with and without rotenone.
Figure 3B:
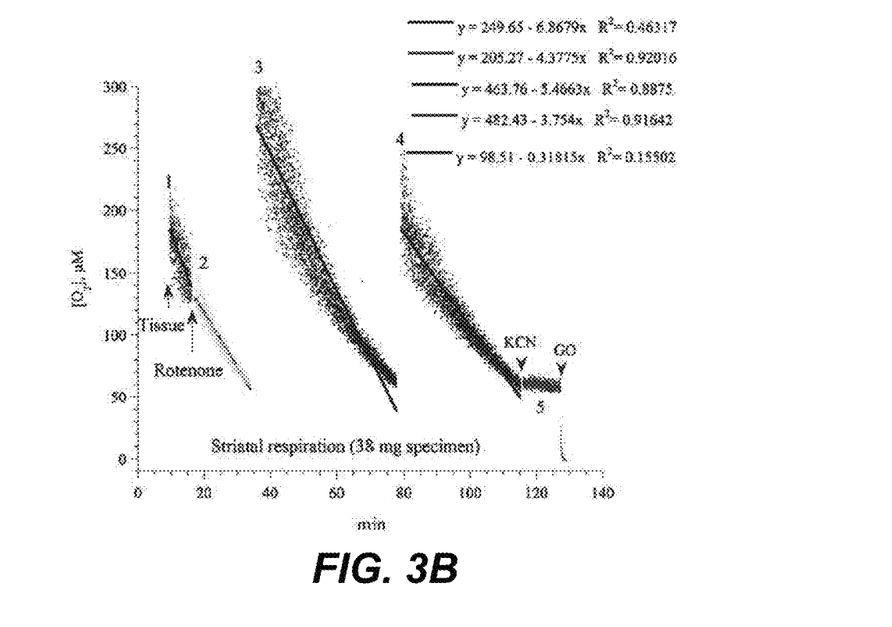
FIG. 3B is a plot of oxygen concentration vs. time with glucose and with repeated additions of rotenone.

Striatal respiration was then studied in the Pd phosphor solution supplemented with 5.0 mM glucose with and without the addition of 10 µM rotenone (FIGS. 3A, 3B). The rate of respiration (k, in µM $O_2$ $min^{-1}$ $mg^{-1}$) in the presence of rotenone was slower (0.092±0.022, n=5, P=0.073), and the curve fitted was more exponential than linear ($R^2$=0.96172 versus $R^2$=0.93107). FIG. 3B shows that the inhibitory effects of rotenone remained relatively stable over about 100 min.

Figure 4A:
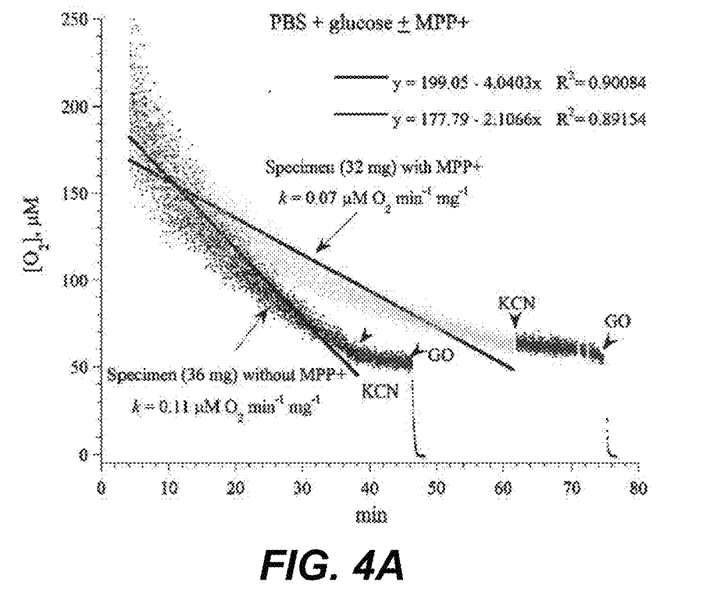
FIG. 4A is a plot of oxygen concentration vs. time without glucose and with and without MPP.
Figure 4B:
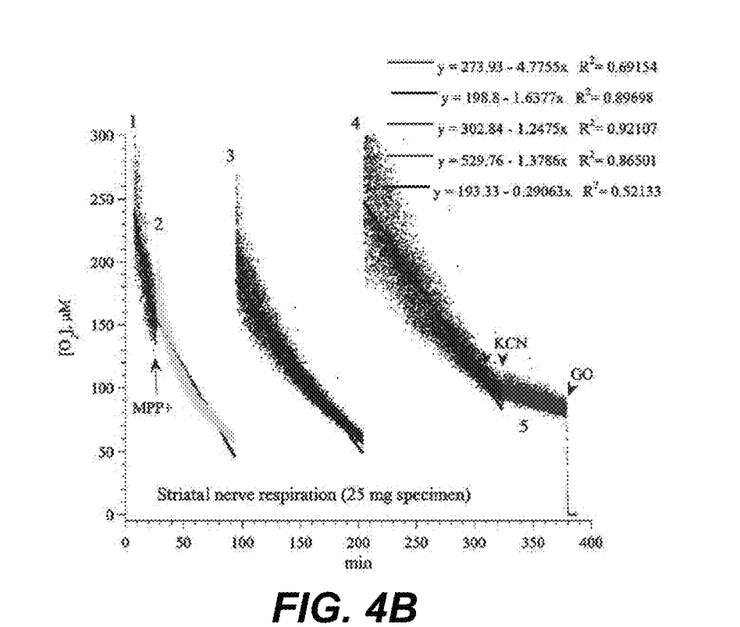
FIG. 4B is a plot of oxygen concentration vs. time with glucose and with repeated additions of MPP.

Striatal respiration was also studied in the Pd phosphor solution supplemented with 5.0 mM glucose with and without the addition of 1.25 mM MPP+ (FIGS. 4A, 4B). The rate of respiration (k, in µM $O_2$ $min^{-1}$ $mg^{-1}$) in the presence of MPP+ was slower (0.077±0.006, n=3, p=0.048) and the curve fitting was more exponential rather than linear ($R^2$=0.90084 versus $R^2$=0.89154). Thus, MPP+ also inhibited the striatal respiration. FIG. 4B shows the inhibitory effects of MPP+ remained relatively stable over about 300 min.

Striatal cellular respiration was linear with time and was inhibited by cyanide, confirming the expected zero-order kinetics of oxygen reduction by cytochrome oxidase in the studied viable tissue. Striatal cellular respiration is also inhibited by rotenone and MPP+, confirming the adverse effects of these known inhibitors of NADH:ubiquinone oxidoreductase on the striatum in vitro. This metabolic event (inhibition of NADH:ubiquinone oxidoreductase) is expected to block NADH (reduced nicotinamide adenine dinucleotide) oxidation, thus depleting cellular NAD+ (oxidized nicotinamide adenine dinucleotide). Briefly, NADH generated in glucose metabolism, especially in the citric acid cycle, must be oxidized to NAD+ by passing its electrons to the electron transport chain and finally to oxygen in the mitochondrial cytochrome oxidase (Complex IV). Inability to regenerate the NAD+ would halt all energy producing reactions, especially in the citric acid cycle.

NAD+, an electron carrier in over 100 major catabolic reactions, has been recently recognized as a principle driver of the glycolysis and citric acid cycle, and a fundamental regulator of the energy metabolism (a bioelectric wire for ATP [adenosine triphosphate] synthase). Likewise, metabolic perturbations affecting NAD+ have been linked to several human diseases, including Parkinson's and Alzheimer's diseases.

Each molecule of NAD+ can accept one hydride ion (a proton and two electrons :$H^-$) in the nicotinamide ring (reversible reduction). The resulting reducing equivalent NADH then wires these electrons to NAD-H:ubiquinone oxidoreductase (dehydrogenation/oxidation), generating an electrochemical potential (electromotive force) across the inner mitochondrial membrane that drives ATP synthesis (phosphorylation). Consequently, inhibitors of NADH:ubiquinone oxidoreductase, such as rotenone and MPP+, are expected to deplete both NAD+ and ATP.

The ratio of NAD+ to NADH in the cell is typically high, favoring hydride transfers by over 200 known oxidoreductases in the main metabolic pathways (e.g., oxidations of pyruvate, fatty acids, α-keto acids) to form NADH. Thus, cellular NAD+ is central in the electron transport that supports oxidative phosphorylation. Future studies, however, are needed to determine whether this metabolic derangement (cellular depletion of NAD+) dominates in both sporadic and genetic forms of Parkinson's disease.

Using the above described method, striatal tissue can be investigated by in vitro exposure of viable tissue to toxins, as shown here. The same approach can also be used by collecting striatal tissue following in vivo treatment of the animal. Use of the phosphorescence oxygen analyzer provides simplicity, low cost, and the ability to monitor respiration over several hours.

In conclusion, we show here that the phosphorescence oxygen analyzer is useful in evaluating the adverse effects of the studied two metabolic poisons on the striatum. Future studies are needed to explore its use as a screening tool for studying the effects of a wide-range of environmental compounds on the striatum.

Example 2

Spinal Cord Bioenergetics in Mice Afflicted with Autoimmune Encephalomyelitis

Pd(II) meso-tetra (sulfophenyl) tetrabenzoporphyrin sodium salt ($C_{60}H_{32}N_4Na_4O_{12}PdS_4$, catalogue number T41161) was purchased from Frontier Scientific (Logan, Utah, USA); it was dissolved in $dH_2O$ (2.5 mg/mL, 2 mM) and stored at −20° C. MOG35-55 (catalogue #AS-60130-5) was purchased from AnaSpec (California, USA) as a lyophilized power (5 mg); it was dissolved in 1.0 mL $dH_2O$ and stored at −20° C. *Mycobacterium tuberculosis* (MTB) strain H37Ra (catalogue #231141) was purchased from Bio-Rad Laboratories (California, USA) as a lyophilized powder and stored at 4° C. Freund's incomplete adjuvant (FIA, catalogue #014H-8800) was purchased from Sigma-Aldrich (St. Louis, Mo.) and stored at 4° C. Pertussis toxin was purchased from Sigma-Aldrich (St. Louis, Mo.) as a 50 µg lyophilized powder (catalogue #P7208), and was dissolved in 1.0 mL $dH_2O$ plus 2 mg/mL bovine serum albumin and stored at 4° C. Its working solution was 6.0 µg pertussis toxin in 10 mL phosphate-buffered saline (PBS). Glucose oxidase (GO; catalogue #G7141) was purchased from Sigma-Aldrich (St. Louis, Mo.); its solution (10 mg/mL) was dissolved in $dH_2O$ and stored at −20° C. Potassium cyanide (KCN, catalogue #10201) was purchased from BDH Middle East LLC (Dubai, UAE); its solution was prepared in $dH_2O$ immediately prior to use. The remaining reagents were purchased from Sigma-Aldrich and prepared and stored as previously described.

C57BL6 female mice (13 weeks old on Day 0; mean±SD weight 20.6±1.4 g, median 21.0 g, range 16.3-22.2 g) were housed at 22° C. with 60% humidity and 12-h light-dark cycles. Rodent chow and filtered water were provided ad libitum. It is well to know that wet rodent chow and filtered water were made always accessible to mice with all disease scores. The study was approved from the UAE University Animal Research Ethics Committee—(Ref. ERA-2019-6026; Bioenergetics of the spinal cord in mice model of chronic and relapsing-remitting EAE [experimental autoimmune encephalomyelitis]).

Sodium pentobarbital (90 µg/g, given intraperitoneally) was used for anesthesia. Mice were monitored daily for weight and clinical signs of disease. Disease severity was scored as: 0, no symptoms; 1, flaccid tail; 2, hind-limb mild weakness (quick righting reflex); 3, hind-limb severe weakness (slow righting reflex); 4, hind-limb paralysis; and 5, hind-limb paralysis and partial forelimb weakness.

The following treatment protocols were employed on Day 0 (>5 mice per group; total mice 35): Group 1 (adjuvant-only control mice): Mice were injected with the adjuvant (FIA) subcutaneously into the base of tail. Groups 2 and 4 (lower-dose of the encephalitogen mice): Mice were injected with 50 µg MOG35-55 plus 0.1 mg MTB subcutaneously into the base of tail or the hind-flank, respectively. Groups 3 and 5 (higher-dose of the encephalitogen mice): Mice were injected with 300 µg MOG35-55 plus 0.4 mg MTB subcutaneously into the base of tail or the hind-flank, respectively.

Groups 2-5 also received 0.3 µg pertussis toxin intraperitoneally on Day 0 and 48 h later.

For Groups 2 and 4, 3.0 mL FIA was emulsified with 3.0 mg MTB and 200 µg MOG35-55; each mouse received a total of 200 µL, 100 µL on each side. For Groups 3 and 5, 3.0 mL FIA was emulsified with 12 mg MTB and 1.2 mg MOG35-55; each mouse received a total of 200 µL, 100 µL on each side.

Fragments from the spinal cord were collected as described below. Briefly, mice were placed on a clean clip board and stabilized by pinning the four flanks. The skin of the back was cleaned with 70% ethanol, and removed to expose the bones. A cut (about 0.5 cm) was made in the lower region to expose the tip of the cord. The bones were dissected on both sides to fully expose the spinal cord. A tweezer was used to remove the entire spinal cord, which was immersed in ice-cold phosphate-buffered saline (PBS: 137 mM NaCl, 2.7 mM KCl, 4.3 mM $Na_2HPO_4$, and 1.4 mM $KH_2PO_4$, pH 7.4) supplemented with 5 mM glucose to rinse the blood. A specimen, (10-40 mg) was then immediately placed in an oxygen measuring vial that contained freshly prepared 2.0 mL PBS, 3 µM Pd phosphor, and 0.5% fat-free albumin, with or without 5 mM glucose. The vial was sealed from air and then placed in the oxygen measuring chamber for determining the rate of respiration at 25° C. Mixing was carried out with the aid of parylene-coated stirring bars.

The previously described phosphorescence oxygen analyzer was used to measure oxygen consumption by the studied spinal cord fragments. The Pd phosphor (absorption maximum at 625 nm; phosphorescence emission maximum at 800 nm) was used for oxygen detection. The measuring glass vials were exposed to 10 per sec light flashes from a pulsed light-emitting diode array with the peak output at 625 nm (OTL630A-5-10-66-E, Opto Technology, Inc., Wheeling, Ill.). Phosphorescence was detected by Hamamatsu photomultiplier tube type 932 (vacuum phototube) after passing through a filter centered at 800 nm. The amplified phosphorescence decay was digitized at 1.0 MHz by a 20-MHz A/D converter (Computer Boards, Inc., Mansfield, Mass.). Respiration was measured at 25° C. in 2-mL sealed glass vials.

The previously described program from Microsoft Visual Basic 6, Microsoft Access Database 2007, and Universal Library components (Universal Library for Measurements Computing Devices) was used for the analysis. The program allowed direct reading from the PCI-DAS 4020/12 I/O Board (PCI-DAS 4020/12 I/O Board). Pulse detection was accomplished by searching for 10 phosphorescence intensities >1.0 volt. Peak detection was accomplished by searching for the highest 10 data points of a pulse and choosing the data point closest to the pulse decay curve. The phosphorescence decay rate (1/r) was a single exponential; $I=Ae^{-t/\tau}$, I=Pd phosphor phosphorescence. The values of $1/\tau$ were linear with dissolved oxygen: $1/\tau=1/\tau°+k_q[O_2]$; $1/\tau$=the phosphorescence decay rate in the presence of $O_2$, $1/\tau°$=the phosphorescence decay rate in the absence of 02, and $k_q$=the second-order $O_2$ quenching rate constant in $s^{-1}$ $µM^{-1}$.

In the reaction vial (sealed from air), oxygen concentration decreased linearly with time, indicating the kinetics of cellular mitochondrial oxygen consumption was zero-order. The rate of respiration (k, in µM $O_2$ $min^{-1}$) was thus the negative of the slope of $d[O_2]/dt$. The calibration reactions contained PBS with 3 µM Pd phosphor, 0.5% fat-free albumin, 50 µg/mL glucose oxidase (catalyzed the reaction: D-glucose+$O_2$→D-glucono-δ-lactone+$H_2O_2$) and various concentrations of β-glucose. Potassium cyanide (KCN, approximately 10 mM, prepared in $dH_2O$) inhibited respiration, confirming oxygen was reduced in the mitochondrial respiratory chain.

ATP concentration was measured using the Enliten ATP Assay System (Bioluminescence Detection Kit, Promega, Madison, Wis.). Briefly, extracted spinal fragments were immediately vortexed vigorously and homogenized in 0.5 mL ice-cold (freshly prepared) 2% trichloroacetic acid for 3 min; the supernatants were then collected by centrifugation (1000×g at 4° C. for 10 min) and stored at −80° C. For the analysis, a 0.1 mL aliquot of the sample was neutralized with 0.9 mL of 100 mM Tris-acetate and 2 mM EDTA, pH 7.75 (final pH, about 8). The luminescence intensity was measured at 25° C. using Glomax Luminometer (Promega, Madison, Wis.) and following the manufacturer's instructions. The ATP standard curve was linear from 0.05 pmol to 0.5 pmol ($R^2$=0.9599). The results are expressed as pmol ATP per mg dry pellet weight.

Data were analyzed using SPSS statistical package (version 20). The nonparametric test (2 independent variables, Mann-Whitney U test, asymptotic 2-sided significance) was used to compare between two groups. The nonparametric test (Kruskal Wallis test, asymptote significance) was used to compare between three or four groups. Two-tailed tests were used. P<0.05 was considered significant.

For spinal cord cellular respiration, initially, representative runs of four different experimental conditions were made with the phosphorescence oxygen analyzer described above. The first run was in Pd phosphor solution only (without added tissue), which demonstrated a negligible drift rate over three hours. Thus, correction for the noise level was unnecessary. This length of phosphorescence signal stability allows an extended monitoring, such as measuring cellular respiration in small samples over several hours. The second run represented spinal cord respiration of a 30-mg specimen in Pd phosphor solution plus potassium cyanide (KCN, a specific inhibitor of cytochrome oxidase and a well-known neurotoxin). The rate in the presence of cyanide is relatively small ($k_{cyanide}$=0.013 µM $O_2$ $min^{-1}$ $mg^{-1}$), reflecting cyanide insensitive respiration. Inhibition of respiration by cyanide confirms oxygen is consumed (reduced) by cytochrome oxidase (Complex IV of mitochondrial respiratory chain). The addition of β-glucose plus glucose oxidase demonstrates the halt of oxygen consumption occurred in the presence of oxygen. It is worth noting that the signal in the presence of β-glucose plus glucose oxidase corresponds to the true zero dissolved oxygen concentration. The third run was spinal cord respiration of a 42-mg specimen in Pd phosphor solution without added glucose (i.e., respiration driven by endogenous cellular nutrients. Its profile fits an exponential curve ($R^2$=0.99162) better than a linear curve ($R^2$=0.89793), likely due to limited nutrients, especially after about 50 minutes. The fourth run was spinal cord respiration of a 25-mg specimen in Pd phosphor solution plus 5 mM glucose (i.e., respiration driven by endogenous cellular nutrients plus cellular influx of the added glucose). This profile is linear ($R^2$=0.94969), and its rate is about 3-fold faster than that without glucose (0.091 versus 0.027 µM $O_2$ $min^{-1}$ $mg^{-1}$). Thus, the presence of glucose has improved spinal cord respiration (tissue viability) quantitatively (faster rate) and qualitatively (improved linear kinetics). It is well to know that the linear decline in oxygen concentration with time reflects the expected zero-order kinetics of oxygen reduction by cytochrome oxidase (a constant amount of oxygen is consumed per minute) and signifies viable samples. Again, the addition of cyanide halted cellular respiration, and the addition of glucose oxidase depleted the remaining oxygen in the solution.

Thereafter, three independent experiments were performed. In these experiments, the reaction mixture was reaerated by transferring the spinal cord specimen to a freshly prepared Pd phosphor solution plus 5 mM glucose when oxygen concentration reached about 100 1.1M. This procedure was repeated a few times over a six hour period. Reasonable tissue viability was maintained over the duration of these experiments.

In order to comprehend the clinical impacts of EAE, weight was monitored over 28 days. Various degrees of initial weight loss (within Days 1 and 5) were present in all groups, including the mice who received incomplete adjuvant only (Group 1). Subsequently, a marked weight loss was evident in the mice who received the encephalitogen in the base of tail (Groups 2-3), especially with the higher dose (Group 3, averaging 23% on Day 13), P<0.001. The weight loss in Group 4 (low-dose encephalitogen in hind-flank) was relatively brief and recovered by Day 10. In contrast, the mice who received high-dose encephalitogen in hind-flank (Group 5) showed a weight gain that peaked on Day 10.

Group 3/mouse 4 developed an excessive weight gain of 47% due to generalized edema and died on Day 10. Group 5/mouse 3 also developed edema (29% weight gain) on Day 10; its weight, however, returned to the baseline on Day 14. Thus, edema appears to be an adverse event of the higher immunogen dosing, and future studies are required to understand its pathogenesis.

We next compared the clinical severity of EAE among treated mice. The onset and severity of the disease also varied significantly between Groups 2 to 5 (P=0.001, Kruskal Wallis test). Overall, the disease score progressed from Days 7-13, and was more prominent in mice who received the higher dose of the encephalitogen compared to those who received the lower dose (P=0.001, Mann-Whitney U test), regardless of the administration route. The onset of disease was also earlier in the mice who received the higher dose.

It is well to note that three mice in Group 5 and one mouse in Group 2 reached a disease score of 4 between Days 14 and 17. None of the studied mice, however, showed signs of disease improvement or recovery within the 28 days. One mouse in Group 1 (received the adjuvant only) developed a weak tail (disease score 1) from Days 11-21.

To test our hypothesis that spinal cord bioenergetics is preserved in EAE, cellular respiration and ATP content were measured in spinal cord specimens from mice with different disease scores. The decline in oxygen concentration with time was linear, reflecting the expected zero-order kinetics of oxygen reduction by cytochrome oxidase (a constant amount of oxygen being consumed per minute). The addition of cyanide halted about 90% of oxygen consumption, confirming oxygen was reduced by cytochrome oxidase. The addition of glucose oxidase depleted the remaining oxygen in the solution. The rate of spinal cord respiration (k, in $\mu M\ O_2\ min^{-1}\ mg^{-1}$, measured on Days 13-28) was not significantly different among the studied groups. Overall, the value of k (mean±SD) in control mice was 0.086±0.024 (n=8) and in symptomatic immunized mice (disease score of >1) was 0.079±0.020 (n=15, P=0.265, Mann-Whitney test). Cellular ATP ($\mu mol\ mg^{-1}$ dry pellet weight; measured on Days 13-28) in control mice was 0.068±0.079 (n=11) and in immunized mice was 0.063±0.061 (n=24, P=0.887, Mann-Whitney U test).

Importantly, spinal cords of mice with disease scores of 1-4 were visually abnormal, showing swellings, loss of integrity, tight adherence to bones, and occasional fragmentations. These visible changes are consistent with the known focal inflammatory changes in this rodent model of multiple sclerosis.

The above described approach allows investigating the effects of cytoprotective (e.g., N-acetylcysteine and other sulfhydryl-containing molecules) and neuroactive compounds on spinal cord viability in vitro. It would also permit studying the adverse effects of neurotoxins (e.g., rotenone) and CNS diseases (including inflammatory and neurodegenerative disorders). This methodology exploits the stability of Pd phosphors and their rapid phosphoresce signals (allowing monitoring fast reactions, such as molecules carried by nanoparticles). Tissues with high metabolic requirements, such as neurons, are especially vulnerable to mitochondrial damage. Consistently, mitochondrial dysfunction has been associated with several CNS pathologies, including the neurodegenerative diseases. For these disorders, cellular mitochondrial oxygen consumption has been adopted as a biomarker for assessing the cellular bioenergetics. This sensitive analyte is altered in many CNS diseases, including Alzheimer (Complex IV), Parkinson (Complex I) and Huntington (Complexes II and III) diseases.

A number of methods have been used for measuring cellular mitochondrial oxygen consumption in neuroscience. Typically, these analytical tools are applicable to cell cultures, cell suspensions, tissue fragments, tissue homogenates in suspension, and isolated mitochondria. Briefly, the multi-well plate reader Seahorse XFe24 Analyzer (Agilent Technologies) and Oroboros $O_2$k-FlouroRespirometer (Oroboros Instruments) are, to some degree, more advanced than the conventional, low-cost Clark oxygen electrode chambers. Nevertheless, these instruments have similar biologic applications and provide comparable yields. The phosphorescence oxygen analyzer, on the other hand, is significantly better in this application. The analyzer provides simplicity of the measurements, stability of the Pd phosphors in solution, low cost (an estimated cost of multiple daily experiments is about $100 per year), reliability and reproducibility of the signals, applicability to studying rapid oxygen reactions (allowing ten oxygen concentration measurements per second), and suitability for monitoring processes over many hours or even days. Future studies are needed to compare the phosphorescence oxygen analyzer with other available techniques.

The main research question in this study is whether in vitro measurements of spinal cord respiration (spinal cord specimens suspended in physiologic solution) is preserved. The results here confirm an unaltered in vitro spinal cord respiration in mice with severe EAE. Thus, the observed mitochondrial dysfunction (mainly reduced inner membrane electrochemical potential) in the previous studies likely reflects adverse events of the neuroinflammation (e.g., inhibition of cellular bioenergetics by intra- and extracellular disease-specific mediators), rather than irreversible mitochondrial damage. This view is consistent with observations from a single patient, suggesting "inflammation alone may be sufficient to cause significant clinical deficits".

In this study, the spinal cord bioenergetics was assessed in groups of mice who received two different encephalitogen doses through two different routes of administration. These treatments produced various clinical severities and forms of the disease. Nevertheless, the results are consistent among the studied groups and disease scores, showing a reasonable conservation of the spinal cord respiration and ATP content, accounting for the known reversible course of the axonal damage in this disease. The results are also consistent with our previous findings in the rat model of EAE, showing reasonably preserved spinal cord bioenergetics in this disease.

A few points however require special emphasis. First, the in vitro results shown here may not correlate with the in vivo status of spinal cord metabolism within cerebrospinal fluid (CSF) that contains inflammatory mediators and their neurotoxic products. Therefore, future studies are needed to determine the effects of the CSF from diseased mice on in vitro measurements of spinal cord respiration.

Second, the previously reported mitochondrial pathology (swollen) and reduced inner membrane electrochemical potential were in focal axon lesions in a spontaneously reversible disease. Our results here show reasonable cellular mitochondrial oxygen consumption and ATP content in the spinal cords despite these previously described disrupted mitochondria. Feasible explanations of the overall findings may include a compensatory increase in the function of intact axonal mitochondria, trafficking of mitochondria into focal axon lesions, and upregulation of the aerobic metabolism. It is important to note that a reversible disease is expected to be coupled to sufficient mitochondrial function.

Third, large intra- and inter-group variations in the studied model of EAE are noted here. Their sources are unknown and their resemblance to the clinical spectrum of multiple sclerosis are also unclear. The need to systematically characterize and standardize the rodent model of EAE is clear. This task allows a more effective extrapolation of the results to the human disease multiple sclerosis. Moreover, disease score does not necessary reflect the severity of the CNS lesions. For example, inspecting the spinal cords clearly distinguishes between disease score 0 and disease scores >1. However, the spinal cord appears the same for scores 1 to 4. Therefore, objectives measures of the clinical disease are necessary.

Fourth, 25C is more suitable than 37° C. for the measurement of spinal cord cellular respiration in vitro. The relatively rapid intracellular nutrient depletion at 25° C. (about 40 min) would have been much faster at 37° C. The respiration was reasonably preserved at 25° C., allowing an accurate determination of its zero-order rates. This inference was evident by the linearity of oxygen consumption with time. It is also well to note that this experimental design is especially important for the measurements made on fragments of the central nervous system, in comparison to those made on cell suspensions. Thus, the union of 'lower temperature' and 'smaller sample size' is essential for the accurate determination of spinal cord respiration. Furthermore, the colorless solution PBS is more suitable than the cell culture media (usually red-colored that is known to change with time) for phosphorescence measurements that utilize a red light (625 nm) for excitation.

It is worth noting that incorporating the cyanide-sensitive respiration rate would have no effect on the final results. Nevertheless, the shown cyanide-insensitive rates produced in this study allow such calculations, if desired. Fifth, autopsies on the rodents that died of complications of EAE may reveal valuable clinical information.

The results here do not exclude mitochondrial pathology in EAE. They rather explain that the overall spinal cord bioenergetics in EAE remain reasonably intact, allowing repair of the axonal damages. Therefore, therapeutic efforts should focus on blocking the inflammatory cascades early in the disease process in order to minimize the spinal cord injury. An overwhelming axonal damage in EAE may overcome the cellular repair capacity. As emphasized previously, the disease is reversible and combined molecularly targeted therapies may be needed to overcome the noted pathology in this disease.

It is important to note that the reliability and reproducibility of cellular ATP determinations are hindered by the rapid cellular ATP hydrolysis before the sample is quenched in the trichloroacetic acid. Therefore, collecting and processing samples for determining ATP quantity require special measures to ensure consistency and efficiency. Although these efforts were implemented here, the variation remained high. Due to this concern, it is preferable to measure the rate of cellular ATP synthesis, rather than cellular ATP content. The rate of cellular ATP synthesis can then be compared with that of cellular respiration (coupled oxidative phosphorylation).

A simple, reliable and reproducible approach for determining oxygen consumption by murine spinal cord specimens in vitro is described in this study. The endogenous nutrients of the spinal cord can support cellular respiration for about 30 minutes. Thereafter, a continual respiration requires added glucose. In the presence of glucose, the kinetics of spinal cord respiration is linear with time (zero-order kinetics) and is inhibited by cyanide. Respiration can be applied as a biomarker for assessing the CNS in health and disease. The described method is also applicable to investigating animal models for various nervous system diseases (as discussed in this study), and exploring the effects of neuroactive compounds on spinal specimens in vitro. The results show preserved spinal cord respiration and ATP content in severe EAE. Interventions need to primarily focus on molecularly targeted therapies that block the intracellular inflammatory cascades in this neuroinflammatory disease of the CNS. In addition, strategies that block the extracellular inflammatory mediators are also needed.

It is to be understood that the phosphorescence oxygen analyzer and uses thereof is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. A phosphorescence oxygen analyzer, comprising:
a light source flashing pulses of light at a controllable rate between one (1) pulse per second and one thousand (1,000) pulses per second;
a test chamber adapted for supporting a sample vial in a path of the flashing pulses of light emitted by the light source;
a phosphorescent probe adapted for mixing with a sample of tissue in the sample vial, the phosphorescent probe absorbing the pulses of light at an absorption wavelength and emitting a pulse of phosphorescent light at an emission wavelength in response thereto out of the test chamber in the presence of oxygen in the sample vial;
a detector positioned in a path of the pulses of phosphorescent light emitted by the phosphorescent probe, the detector converting the pulses of phosphorescent light to an electrical waveform having peaks at a frequency identical to the frequency of the pulses of phosphorescent light and an amplitude proportional to intensity of the pulses of phosphorescent light;
an analog-to-digital converter connected to the detector, the analog-to-digital converter converting the electrical waveform from the detector into a digital signal having a stream of pulses, counting the frequency of the stream of pulses and measuring the amplitude and duration of each of the pulses; and a processing unit connected to the analog-to-digital converter, the processing unit having a processor calculating oxygen concentration in the sample vial and rate of decay of the phosphorescent emissions from the phosphorescent probe by comparison to calibration data in memory accessible to the processing unit.

2. The phosphorescence oxygen analyzer according to claim 1, further comprising a high-speed mixer connected to said test chamber for mixing the phosphorescent probe with the tissue sample at a rate compatible with the pulses of light emitted by said light source.

3. The phosphorescence oxygen analyzer according to claim 2, wherein said mixer comprises a resonant acoustic mixer.

4. The phosphorescence oxygen analyzer according to claim 1, wherein said phosphorescent probe comprises a palladium II complex of meso-tetra-(4-sulfonatophenyl)tetrabenzoporphyrin, having an absorption wavelength of 625 nm and an emission wavelength of 800 nm.

5. The phosphorescence oxygen analyzer according to claim 4, further comprising a filter centered around 800 nm disposed in the path of the pulses of phosphorescent light between the sample vial and the detector.

6. The phosphorescence oxygen analyzer according to claim 1, further comprising a temperature control attached to said test chamber.

7. The phosphorescence oxygen analyzer according to claim 6, wherein said temperature control comprises a precision incubator for controlling temperature of reactions occurring in the sample vial.

8. The phosphorescence oxygen analyzer according to claim 1, further comprising a carousel adapted for supporting multiple samples vials and rotating user selectable sample vials into the path of the pulses of light from said light source.

9. The phosphorescence oxygen analyzer according to claim 1, wherein said light source comprises an LED array.

10. A method of assessing effects of environmental toxins on cellular respiration in striatal tissue, comprising the steps of:

extracting samples of striatal tissue from laboratory mice;

mixing one of the striatal tissue samples with a phosphorescent probe, β-glucose and glucose oxidase in a sample vial to form a calibration solution;

using the phosphorescence oxygen analyzer according to claim 1 to measure the rate of decline in oxygen concentration in the calibration solution and saving the measurements as calibration data in memory accessible to the processing unit of the phosphorescence oxygen analyzer;

mixing one of the striatal tissue samples with a phosphorescent probe, glucose, and a dose of an environmental toxin in a glass vial in order to form a test solution;

using the phosphorescence oxygen analyzer according to claim 1 to measure the rate of decline in oxygen concentration in the test solution, the analyzer comparing the rate of decline in oxygen concentration in the test solution with the rate of decline in oxygen concentration in the calibration solution; and assessing cellular respiration in the striatal tissue as impaired by the environmental toxin when the rate of decline in oxygen concentration in the test solution is slower than the rate of decline in oxygen concentration in the calibration solution.

11. The method of assessing effects of environmental toxins on cellular respiration in striatal tissue according to claim 10, wherein the environmental toxin is rotenone.

12. The method of assessing effects of environmental toxins on cellular respiration in striatal tissue according to claim 10, wherein the environmental toxin is 1-methyl-4-phenylpyridinium (MPP).

13. A method of assessing spinal cord bioenergetics in experimental autoimmune encephalomyelitis, comprising the steps of:

extracting control samples of spinal cord tissue from laboratory mice without experimental autoimmune encephalomyelitis;

extracting test samples of spinal cord tissue from laboratory mice after inducing experimental autoimmune encephalomyelitis in the mice;

mixing one of the spinal cord tissue control samples with a phosphorescent probe, β-glucose and glucose oxidase in a sample vial to form a calibration solution;

using the phosphorescence oxygen analyzer according to claim 1 to measure the rate of decline in oxygen concentration in the calibration solution and saving the measurements as calibration data in memory accessible to the processing unit of the phosphorescence oxygen analyzer;

mixing one of the spinal cord tissue test samples with a phosphorescent probe, glucose, and a dose of an environmental toxin in a glass vial in order to form a test solution;

using the phosphorescence oxygen analyzer according to claim 1 to measure the rate of decline in oxygen concentration in the test solution, the analyzer comparing the rate of decline in oxygen concentration in the test solution with the rate of decline in oxygen concentration in the calibration solution; and assessing spinal cord bioenergetics in the spinal cord tissue of the mice having induced experimental autoimmune encephalomyelitis as unaffected by the experimental autoimmune encephalomyelitis when the rate of decline in oxygen concentration in the test solution is not significantly different than the rate of decline in oxygen concentration in the calibration solution.

14. The method of assessing spinal cord bioenergetics in experimental autoimmune encephalomyelitis according to claim 13, wherein said step of inducing experimental autoimmune encephalomyelitis in the mice comprises injecting an encephalitogen in the mouse's tail, followed by injecting pertussis toxin into the mouse.

15. The method of assessing spinal cord bioenergetics in experimental autoimmune encephalomyelitis according to claim 13, wherein said step of inducing experimental autoimmune encephalomyelitis in the mice comprises injecting an encephalitogen in the mouse's hind quarter, followed by injecting pertussis toxin into the mouse.

16. The method of assessing spinal cord bioenergetics in experimental autoimmune encephalomyelitis according to claim 13, further comprising the step of assaying ATP levels in the control samples and the test samples of spinal cord tissue.

* * * * *